(12) United States Patent
Liu

(10) Patent No.: US 9,788,576 B2
(45) Date of Patent: Oct. 17, 2017

(54) ELECTRONIC CIGARETTE, AND BATTERY ROD AND ATOMIZER

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD. SHENZHEN, Guangdong (CN)

( * ) Notice: Subject to any disclaimer, the term of this patent is extended or adjusted under 35 U.S.C. 154(b) by 0 days.

(21) Appl. No.: 14/364,078

(22) PCT Filed: Jan. 13, 2014

(86) PCT No.: PCT/CN2014/070501
§ 371 (c)(1),
(2) Date: Jun. 10, 2014

(87) PCT Pub. No.: WO2015/100789
PCT Pub. Date: Jul. 9, 2015

(65) Prior Publication Data
US 2016/0286858 A1    Oct. 6, 2016

(30) Foreign Application Priority Data

Dec. 30, 2013    (CN) .................. 2013 2 0882290 U

(51) Int. Cl.
*A24F 47/00*    (2006.01)
*H01M 2/02*    (2006.01)
(Continued)

(52) U.S. Cl.
CPC ........... *A24F 47/008* (2013.01); *H01M 2/022* (2013.01); *H01M 10/0422* (2013.01);
(Continued)

(58) Field of Classification Search
None
See application file for complete search history.

(56) References Cited

U.S. PATENT DOCUMENTS 1,862,133 A * 6/1932 Bayan .................. A24D 1/14
                                                          131/226
5,404,891 A * 4/1995 Kiribuchi .............. A24D 1/10
                                                          131/337
(Continued)

FOREIGN PATENT DOCUMENTS

CN    101822420 A    9/2010
CN    202311183    *  7/2012
(Continued)

OTHER PUBLICATIONS

Chinese International Search Report corresponding with PCT Application No. PCT/CN2014070501, dated Oct. 10, 2014, 5 pp.

*Primary Examiner* — Joseph S Del Sole
*Assistant Examiner* — Manley Cummins, IV
(74) *Attorney, Agent, or Firm* — Ohlandt, Greeley, Ruggiero & Perle, LLP

(57) ABSTRACT

An electronic cigarette, and a battery rod and an atomizer thereof are provided in the present application. The battery rod includes a battery rod body, and an air passage of the battery rod body is provided with a waterproof breathable component which cooperates with the air passage and is configured to prevent water from entering into the battery rod body via the air passage, and the atomizer includes an atomizer body, a smoke passage of the atomizer body is provided with a waterproof breathable component which cooperates with the smoke passage and is configured to prevent water from entering into the atomizer body via the smoke passage. Besides of ensuring the breathability of both the air passage and the smoke passage, the waterproof breathable component may also prevent external liquid from entering into the battery rod and the atomizer, thus the waterproof performance of the electronic cigarette is improved.

7 Claims, 6 Drawing Sheets

(51) Int. Cl.
   *H01M 10/04*     (2006.01)
   *A61M 11/00*     (2006.01)
   *A61M 16/00*     (2006.01)
   *A61M 15/06*     (2006.01)
   *A61M 15/00*     (2006.01)

(52) U.S. Cl.
   CPC ............. *A61M 11/00* (2013.01); *A61M 15/00* (2013.01); *A61M 15/06* (2013.01); *A61M 16/00* (2013.01); *H01M 2220/30* (2013.01)

(56) References Cited

U.S. PATENT DOCUMENTS

| | | | |
|---|---|---|---|
| 8,905,040 B2* | 12/2014 | Scatterday | A61M 15/06 128/202.21 |
| 2012/0111346 A1* | 5/2012 | Rinker | A24F 47/002 131/328 |
| 2012/0204889 A1* | 8/2012 | Xiu | A24F 47/008 131/273 |
| 2013/0081642 A1* | 4/2013 | Safari | A24F 47/008 131/329 |
| 2013/0213419 A1 | 8/2013 | Tucker et al. | |
| 2014/0334803 A1* | 11/2014 | Li | H05B 3/03 392/394 |

FOREIGN PATENT DOCUMENTS

| | | |
|---|---|---|
| CN | 202311183 U | 7/2012 |
| CN | 203194539 U | 9/2013 |
| CN | 203327951 U | 12/2013 |
| KR | 2012008751 | 12/2012 |
| KR | 20130133711 A | 12/2013 |

* cited by examiner

ELECTRONIC CIGARETTE, AND BATTERY ROD AND ATOMIZER

The present application is the national phase of International Application No. PCT/CN2014/070501, titled "ELECTRONIC CIGARETTE, AND BATTERY ROD AND ATOMIZER THEREOF", filed on Jan. 13, 2014, which claims the benefit of priority to Chinese Patent Application No. 201320882290.8, entitled "ELECTRONIC CIGARETTE, AND BATTERY ROD AND ATOMIZER THEREOF", filed with the Chinese State Intellectual Property Office on Dec. 30, 2013, both of which applications are incorporated herein in their entireties by this reference.

FIELD

The present application relates to the technical field of electronic cigarette parts, in particular to a battery rod and an atomizer. The present application further relates to an electronic cigarette having the battery rod and the atomizer.

BACKGROUND

An electronic cigarette is a common electronic simulation cigarette product. As a main structural component, a battery rod plays an important role in the whole working effect of the electronic cigarette. However, with the continuous increasing of requirements for production and use, a higher performance of the battery rod is required.

At present, the existing electronic cigarette generally includes an atomizer and a battery rod, the atomizer and the battery rod are detachably connected or non-detachably connected, and the electronic cigarette having an atomizer and a battery rod which are non-detachably connected, is also referred to as a disposable electronic cigarette. A smoke passage configured to allow smoke to flow is provided in the atomizer and extends in an axial direction, and an air passage is provided in the battery rod in an axial direction and is communicated with the smoke passage. During the operation of the electronic cigarette, the airflow entered in the air passage flows into the smoke passage and is mixed with the smoke in the smoke passage, and then the mixture of smoke and air is sent into the user's mouth.

However, neither the battery rod nor the atomizer have any waterproof structure or waterproof assembly, thus in a case that the battery rod or the atomizer is soaked with water, water generally enters into the insides of the battery rod and the atomizer via the air passage and the smoke passage, respectively, which may cause a short circuit of the electronic cigarette, thus the electronic cigarette can not work normally and the soaked battery rod is prone to be broken, thereby causing inconvenience to the normal use of the electronic cigarette. Furthermore, a taste of the smoke may be changed when the water in the electronic cigarette is mixed with the cigarette liquid in the electronic cigarette, thus the taste is adversely affected.

Therefore, an important technical issue to be solved at present by those skilled in the art is to improve a waterproof performance of the battery rod.

SUMMARY

An object of the present application is to provide a battery rod and an atomizer which both have a great waterproof performance. Another object of the present application is to provide an electronic cigarette having the battery rod and the atomizer.

In order to address the technical issues, a battery rod, configured to form an electronic cigarette in combination with an atomizer, is provided in the present application, and includes a battery rod body, an air passage is provided inside the battery rod body in an axial direction of the battery rod body and is configured to allow airflow to flow and to convey the airflow into the atomizer, and the air passage is provided with a waterproof breathable component which cooperates with the air passage and is configured to prevent water from entering into the battery rod body via the air passage.

Preferably, the battery rod body includes a sleeve, and an end cover and a connecting member arranged at two ends of the sleeve, the connecting member is configured to connect the atomizer, an air inlet of the air passage is arranged at one end, away from the connecting member, of the battery rod body, and the waterproof breathable component is arranged at an inner side of the end cover.

Preferably, the waterproof breathable component is a waterproof breathable membrane.

Preferably, the waterproof breathable component is a high molecular weight polyethylene waterproof breathable membrane or a polytetrafluoroethylene waterproof breathable membrane.

Preferably, the waterproof breathable component is arranged at an inner side or an outer side of the air inlet of the air passage.

An atomizer is further provided according to the present application, and is configured to form an electronic cigarette in combination with a battery rod, wherein the atomizer includes an atomizer body, a smoke passage configured to allow smoke to flow is provided inside the atomizer body in an axial direction of the atomizer body, and the smoke passage is provided with a waterproof breathable component which cooperates with the smoke passage and is configured to prevent water from entering into the atomizer body via the smoke passage.

Preferably, the atomizer body is provided with a mouthpiece end, and a connecting end configured to connect the battery rod, and the waterproof breathable component is arranged at the mouthpiece end of the atomizer.

Preferably, the waterproof breathable component is a high molecular weight polyethylene waterproof breathable membrane or a polytetrafluoroethylene waterproof breathable membrane.

An electronic cigarette is further provided according to the present application, and includes a battery rod and an atomizer which are connected to each other, the battery rod is the battery rod according to any one of the above-described solutions, and the atomizer is the atomizer according to any one of the above-described solutions.

Preferably, the battery rod, and the atomizer are of a non-detachable integrated structure.

Compare with the background technology, in the battery rod, the atomizer and the electronic cigarette provided in the present application, the air passage of the battery rod is provided with the waterproof breathable component which cooperates with the air passage and is configured to prevent water from entering into the battery rod body via the air passage, and the smoke passage of the atomizer is provided with the waterproof breathable component which cooperates with the smoke passage and is configured to prevent water from entering into the atomizer body via the smoke passage. Thus, besides of ensuring the breathability of both the air passage and the smoke passage, the waterproof breathable component may also effectively isolate external liquid, such as water, and prevent the external liquid, such as water, from entering into the battery rod body and the atomizer body, thus the waterproof performance of the battery rod may be effectively improved, the whole waterproof performance of the electronic cigarette is correspondingly improved, which may avoid a short circuit caused in a case that the external water enters into the inside of the electronic cigarette and a change of smoke taste caused by the mixing of water and cigarette liquid. Thus, the electronic cigarette may be used in an environment with much water, such as in the rain, a bathroom or a swimming pool, which broadens the application scope of the electronic cigarette, improves the user experience and facilitates the popularization and application of the electronic cigarette.

BRIEF DESCRIPTION OF THE DRAWINGS

For more clearly illustrating embodiments of the present application or the technical solution in the conventional technology, drawings referred to describe the embodiments or the conventional technology is briefly described hereinafter. Apparently, the drawings in the following description are only a few of embodiments of the present application, and for those skilled in the art other drawings may be obtained based on these drawings without any creative efforts.

DETAILED DESCRIPTION OF THE PREFERRED EMBODIMENTS

A battery rod having a great waterproof performance is provided in the present application; and an atomizer having a great waterproof performance and an electronic cigarette having the battery rod and the atomizer are further provided in the present application.

For those skilled in the art to better understand technical solutions of the present application, the present application is described in detail in conjunction with drawings and embodiments hereinafter.

Figure 1:
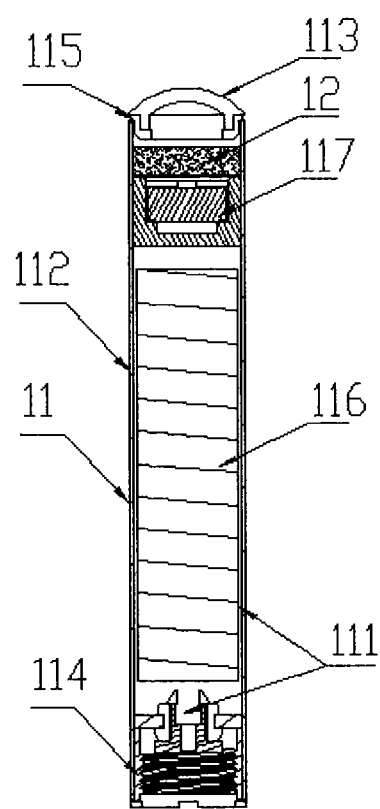
FIG. 1 is an assembling structural schematic view of a first structure of a battery rod according to an embodiment of the present application.

Reference is made to FIG. 1, which is an assembling structural schematic view of a first structure of a battery rod according to an embodiment of the present application.

In an embodiment, the battery rod according to the present application is configured to form an electronic cigarette in combination with an atomizer, and includes a battery rod body 11. An air passage 111 is provided inside the battery rod body 11 in an axial direction of the battery rod body 11 and is configured to allow airflow to flow and to convey the airflow into the atomizer. The air passage 111 is provided with a waterproof breathable component 12 which cooperates with the air passage 111 and is configured to prevent water from entering into the battery rod body 11 via the air passage 111.

In a working process, besides of ensuring the breathability of the air passage 111, the waterproof breathable component 12 may also effetely isolate external liquid, such as water, and prevent the external liquid, such as water, from entering into the battery rod, thus the waterproof performance of the battery rod may be effectively improved, and the whole waterproof performance of the electronic cigarette is correspondingly improved, which may avoid a short circuit caused in a case that the external water enters into the inside of the electronic cigarette. Thus, the electronic cigarette may be used in an environment with much water, such as in the rain, a bathroom or a swimming pool, which broadens the application scope of the electronic cigarette, improves the user experience and facilitates the popularization and application of the electronic cigarette.

Further, the battery rod body 11 includes a sleeve 112, and an end cover 113 and a connecting member 114 arranged at two ends of the sleeve 112, respectively. The connecting member 114 is configured to connect the atomizer and is provided with internal threads to realize a connection with the atomizer by threaded connection. It should be understood that, the connection manner between the connecting member 114 and the atomizer may be clamping connection, magnetic connection or tight fit connection, which is not limited herein.

An air inlet 115 of the air passage 111 is arranged at one end, away from the connecting member 114, of the battery rod body 11, and the waterproof breathable component 12 is arranged at an inner side of the end cover 113. Furthermore, a battery 116 and a control module 117 are provided inside the battery rod body 11, and the control module 117 is configured to control the battery 116 to supply power to the atomizer, and the above components are conventional technologies, thus will not be described herein. A flow path of the airflow in the air passage 111 in this embodiment is described as follows. The airflow enters into the waterproof breathable component 12 via the air inlet 115, then passes through an air hole (not shown) of the control module 117, and then passes through a gap between the sleeve 112 and the battery 116, and finally flows out via the connecting member 114.

In this embodiment, the air inlet 115 is arranged on the end cover 113, and apparently, the air inlet 115 may also be arranged on the sleeve 112, or a gap between the sleeve 112 and the end cover 113 may form the air inlet 115, which is not limited herein. The waterproof breathable component 12 may also be directly arranged at an inner side or an outer side of the air inlet 115 of the air passage 111, which is not limited herein.

The waterproof breathable component 12 is preferably a waterproof breathable membrane, and is more preferably a high molecular weight polyethylene waterproof breathable membrane or a polytetrafluoroethylene waterproof breathable membrane. It should be noted that, the waterproof breathable component 12 being a high molecular weight polyethylene waterproof breathable membrane or a polytetrafluoroethylene waterproof breathable membrane is merely a preferable solution, and the waterproof breathable component 12 is not limited to that, and may be of other materials, as long as it can meet the practical requirement of the battery rod. The high molecular weight polyethylene waterproof breathable membrane and the polytetrafluoroethylene waterproof breathable membrane are both an existing material on sale in the market, thus the structure and principle thereof will not be described herein.

Figure 2:
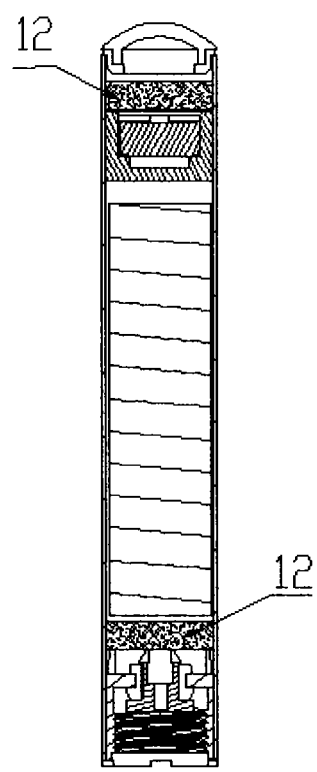
FIG. 2 is an assembling structural schematic view of a second structure of a battery rod according to an embodiment of the present application.

Reference is made to FIG. 2, which is an assembling structural schematic view of a second structure of a battery rod according to an embodiment of the present application. This embodiment has a similar structure as the first embodiment, and unlike the first embodiment, in this embodiment, a waterproof breathable component 12 is further arranged at an inner side of the connecting member 114 of the battery rod body 11. Such structure may ensure both ends of the battery rod body 11 are waterproof, thus before the battery rod body 11 is combined with the atomizer, such structure may better prevent water from entering into the battery rod body 11, thereby further improving the waterproof performance of the battery rod body.

Figure 3:
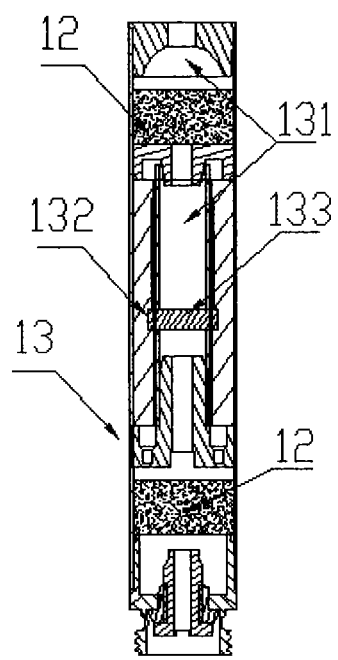
FIG. 3 is an assembling structural schematic view of a first structure of an atomizer according to an embodiment of the present application.

Referring to FIG. 3, an atomizer according to the present application is configured to form an electronic cigarette in combination with a battery rod, and includes an atomizer body 13. A smoke passage 131 configured to allow smoke to flow is provided inside the atomizer body 13 in an axial direction of the atomizer body 13, and the smoke passage 131 is provided with a waterproof breathable component 12 which cooperates with the smoke passage 131 and is configured to prevent water from entering into the atomizer body 13 via the smoke passage 131. The atomizer according to the present application may avoid a short circuit caused in a case that the external water enters into the atomizer and a change of smoke taste caused by the mixing of water and cigarette liquid. Thus, the atomizer may be used in an environment with much water, such as in the rain, a bathroom or a swimming pool, which broadens the application scope of the electronic cigarette, improves the user experience and facilitates the popularization and application of the electronic cigarette.

Figure 4:
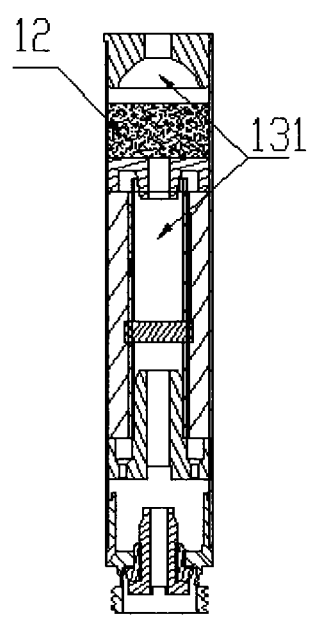
FIG. 4 is an assembling structural schematic view of a second structure of an atomizer according to an embodiment of the present application.

The atomizer body 13 is provided with a mouthpiece end, and a connecting end configured to connect the battery rod. Inner sides of the mouthpiece end and the connecting end are each provided with a waterproof breathable component 12. A liquid storage component 132 for storing cigarette liquid and an atomizing assembly 133 for atomizing the cigarette liquid are provided between the two waterproof breathable components 12, and the atomizing assembly 133 includes an electric heating wire and a liquid guiding wick for guiding liquid towards the electric heating wire. The liquid storage component 132 and the atomizing assembly 133 are both conventional technologies, which will not be described herein. It can be understood that, in another embodiment as shown in FIG. 4, the waterproof breathable component 12 may only be arranged at the mouthpiece end of the atomizer to improve the ventilation effect and save cost. The waterproof breathable component 12 in the atomizer may be a high molecular weight polyethylene waterproof breathable membrane or a polytetrafluoroethylene waterproof breathable membrane, and may also be of other materials as long as it meets the requirement of waterproof and breathable, which is not limited herein.

An electronic cigarette is further provided in the present application, and includes a battery rod and an atomizer which are connected to each other, the battery rod is the battery rod described above, and the atomizer is the atomizer described above. The battery rod and the atomizer are detachably connected. Since the battery rod and the atomizer of the electronic cigarette, respectively, have the same structures as those of the battery rod and the atomizer which are described above, the electronic cigarette has a corresponding waterproof effect. In order to save cost and realize a better ventilation effect, only an inner side of the mouthpiece end of the atomizer and an inner side of the end cover of the battery rod are each provided with a waterproof breathable component 12. Apparently, end covers at both ends of the electronic cigarette may be directly provided as the waterproof breathable component, which is not limited herein.

Figure 5:
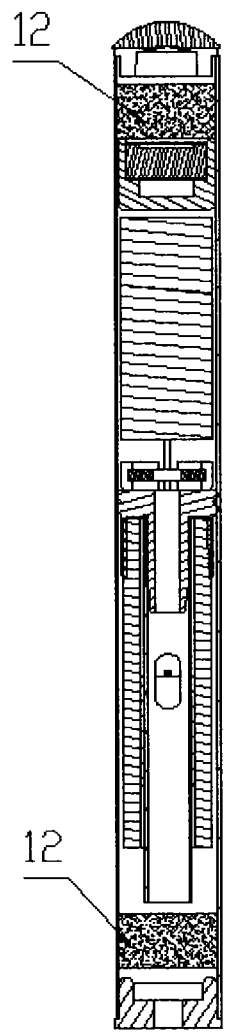
FIG. 5 is an assembling structural schematic view of a structure of an electronic cigarette according to an embodiment of the present application.

Reference is made to FIG. 5, which is an assembling structural schematic view of a structure of an electronic cigarette according to an embodiment of the present application. This embodiment has the similar structure as that of the embodiment described above, and unlike the above embodiment, in this embodiment, the battery rod and the atomizer are of a non-detachable integrated structure. Inner sides of two ends of the electronic cigarette are each provided with a waterproof breathable component 12.

Figure 6:
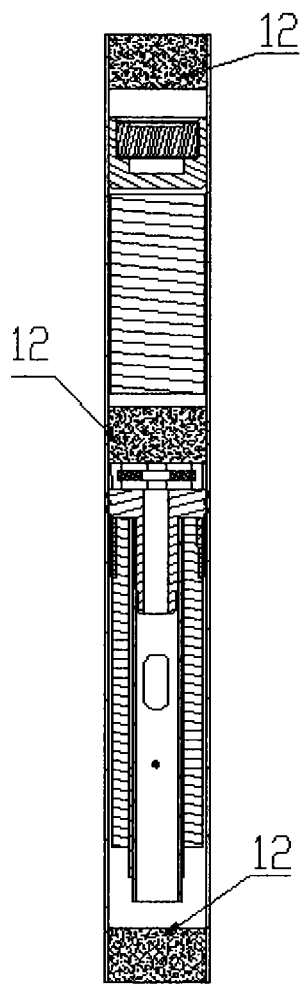
FIG. 6 is an assembling structural schematic view of another structure of an electronic cigarette according to an embodiment of the present application.

Reference is made to FIG. 6, which is an assembling structural schematic view of another structure of an electronic cigarette according to an embodiment of the present application. This embodiment has the similar structure as that of the embodiment described above, and unlike the above embodiment, in this embodiment, end covers at both ends of the electronic cigarette are each provided with a waterproof breathable component 12, and a waterproof breathable component 12 for preventing cigarette liquid from entering into the battery rod is further provided between the atomizer and the battery rod. The electronic cigarette has a better waterproof and oil proof performance.

In conclusion, in the battery rod, the atomizer and the electronic cigarette provided in the present application, the air passage 111 of the battery rod is provided with the waterproof breathable component 12 which cooperates with the air passage 111 and is configured to prevent water from entering into the battery rod body 11 via the air passage 111, and the smoke passage 131 of the atomizer is provided with the waterproof breathable component 12 which cooperates with the smoke passage 131 and is configured to prevent water from entering into the atomizer body 13 via the smoke passage 131. Thus, besides of ensuring the breathability of both the air passage 111 and the smoke passage 131, the waterproof breathable component 12 may also effectively isolate external liquid, such as water, and prevent the external liquid, such as water, from entering into the battery rod body 11 and the atomizer body 131, thus the waterproof performances of the battery rod, the atomizer and the electronic cigarette may be effectively improved, the whole waterproof performance of the electronic cigarette is correspondingly improved, which may avoid a short circuit caused in a case that the external water enters into the inside of the electronic cigarette and a change of smoke taste caused by the mixing of water and cigarette liquid. Thus, the electronic cigarette may be used in an environment with much water, such as in the rain, a bathroom or a swimming pool, which broadens the application scope of the electronic cigarette, improves the user experience and facilitates the popularization and application of the electronic cigarette.

A battery rod and an electronic cigarette having the battery rod provided in the present application are described in detail hereinbefore. The principle and the embodiments of the present application are illustrated herein by specific examples. The above description of examples is only intended to help the understanding of the method and idea of the present application. It should be noted that, for the person skilled in the art, modifications and improvements may be made to the present application without departing from the principle of the present application, and these modifications and improvements are also deemed to fall into the scope of the present application defined by the claims.

What is claimed is:

1. An electronic cigarette, comprising a battery rod and an atomizer which are connected to each other, wherein the battery rod comprises a battery rod body, an air passage is provided inside the battery rod body in an axial direction of the battery rod body and is configured to allow airflow to flow and to convey the airflow into the atomizer, and the air passage is provided with a first waterproof breathable component which cooperates with the air passage and is configured to prevent water from entering into the battery rod body via the air passage; and the atomizer comprises an atomizer body, a smoke passage configured to allow smoke to flow is provided inside the atomizer body in an axial direction of the atomizer body, and the smoke passage is provided with a second waterproof breathable component which cooperates with the smoke passage and is configured to prevent water from entering into the atomizer body via the smoke passage.

2. The electronic cigarette according to claim 1, wherein the battery rod and the atomizer are of a non-detachable integrated structure.

3. The electronic cigarette according to claim 1, wherein the battery rod body comprises a sleeve, and an end cover and a connecting member arranged at two ends of the sleeve, the connecting member is configured to connect the atomizer, an air inlet of the air passage is arranged at one end, away from the connecting member, of the battery rod body, and the first waterproof breathable component of the battery rod is arranged at an inner side of the end cover.

4. The electronic cigarette according to claim 1, wherein the first waterproof breathable component and the second waterproof breathable component are each a waterproof breathable membrane.

5. The electronic cigarette according to claim 4, wherein the waterproof breathable membrane is a polyethylene waterproof breathable membrane or a polytetrafluoroethylene waterproof breathable membrane.

6. The electronic cigarette according to claim 1, wherein the first waterproof breathable component of the battery rod is arranged at an inner side or an outer side of an air inlet of the air passage.

7. The electronic cigarette according to claim 1, wherein the atomizer body is provided with a mouthpiece end, and a connecting end configured to connect the battery rod, and the second waterproof breathable component of the atomizer is arranged at the mouthpiece end of the atomizer.

* * * * *

UNITED STATES PATENT AND TRADEMARK OFFICE
CERTIFICATE OF CORRECTION

PATENT NO. : 9,788,576 B2
APPLICATION NO. : 14/364078
DATED : October 17, 2017
INVENTOR(S) : Qiuming Liu Page 1 of 1

It is certified that error appears in the above-identified patent and that said Letters Patent is hereby corrected as shown below:

On the Title Page

Column 1
Item (73) please add "HUIZHOU KIMREE TECHNOLOGY CO., LTD. SHENZHEN BRANCH"

Signed and Sealed this
Twelfth Day of March, 2019

Andrei Iancu
*Director of the United States Patent and Trademark Office*